United States Patent [19]

Sittler et al.

[11] Patent Number: 4,909,078
[45] Date of Patent: Mar. 20, 1990

[54] FLUID FLOW DETECTOR

[75] Inventors: Fred C. Sittler, Excelsior, Minn.; James H. Crabtree, Long Beach, Calif.

[73] Assignee: Rosemount Inc., Eden Prairie, Minn.

[21] Appl. No.: 108,487

[22] Filed: Oct. 14, 1987

[51] Int. Cl.$^4$ .............................................. G01F 1/68
[52] U.S. Cl. .............................. 73/204.26; 73/204.21; 73/27 R; 338/25; 338/318
[58] Field of Search ............ 73/23, 27 R, 204, 204.25, 73/204.26, 204.27, 204.21; 338/25, 283, 284, 318, 319

[56] References Cited

U.S. PATENT DOCUMENTS

| Re. 30,105 | 10/1979 | Rodder | 73/204 X |
|---|---|---|---|
| 3,988,928 | 11/1976 | Edstrom et al. | 73/204 |
| 4,332,157 | 6/1982 | Zemel et al. | 73/26 |
| 4,343,768 | 8/1982 | Kimura | 73/204 X |
| 4,471,647 | 9/1984 | Jerman et al. | 73/23 |
| 4,472,239 | 9/1984 | Johnson et al. | 156/647 |
| 4,474,889 | 10/1984 | Terry et al. | 436/161 |
| 4,478,076 | 10/1984 | Bohrer | 73/204 |
| 4,478,077 | 10/1984 | Bohrer et al. | 73/204 |
| 4,501,144 | 2/1985 | Higashi et al. | 73/204 |
| 4,502,339 | 3/1985 | Horn | 73/204 X |
| 4,537,068 | 8/1985 | Wrobel et al. | 73/202 |
| 4,542,650 | 9/1985 | Renken et al. | 73/204 |
| 4,548,078 | 10/1987 | Bohrer et al. | 73/204 |
| 4,561,303 | 12/1985 | McCarthy | 73/204 |
| 4,576,050 | 3/1986 | Lambert | 73/861 |
| 4,580,439 | 4/1986 | Manaka | 73/23 |
| 4,587,843 | 5/1986 | Tokura et al. | 73/204 |
| 4,594,889 | 6/1986 | McCarthy | 73/204 |
| 4,608,865 | 9/1986 | Muller et al. | 73/204 |
| 4,624,137 | 11/1986 | Johnson et al. | 73/204 |
| 4,624,138 | 11/1986 | Ono et al. | 73/204 |
| 4,627,279 | 12/1986 | Ohta et al. | 73/195 |
| 4,633,578 | 1/1987 | Aine et al. | 73/204 X |
| 4,651,564 | 3/1987 | Johnson et al. | 73/204 |
| 4,658,855 | 4/1987 | Doyle | 137/468 |
| 4,685,331 | 8/1987 | Renken | 73/204 |

OTHER PUBLICATIONS

Description of "Chromatography", *Encyclopedia of Instrumentation and Control*, D. M. Considine, pp. 128-136.

Primary Examiner—Herbert Goldstein
Attorney, Agent, or Firm—Kinney & Lange

[57] ABSTRACT

A thermal effect sensing device comprises a semiconductor substrate supporting an insulating layer which has a thin film of platinum deposited on it. Holes are etched through the semiconductor substrate and the insulating layer. The platinum film is shaped to provide a serpentine resistive element suspended over one of the holes. The serpentine element is suspended from the rim of the hole, but is otherwise unsupported. The resistive element has a low thermal mass and there is a low thermal resistance between the element and fluid in the sensor. The sensor senses thermal properties of the fluid in the sensor, such as mass flow or thermal conductivity. A second conductive film is insulatingly deposited on the first film to provide a resistive sensor electrically isolated from a resistive heating element.

13 Claims, 5 Drawing Sheets

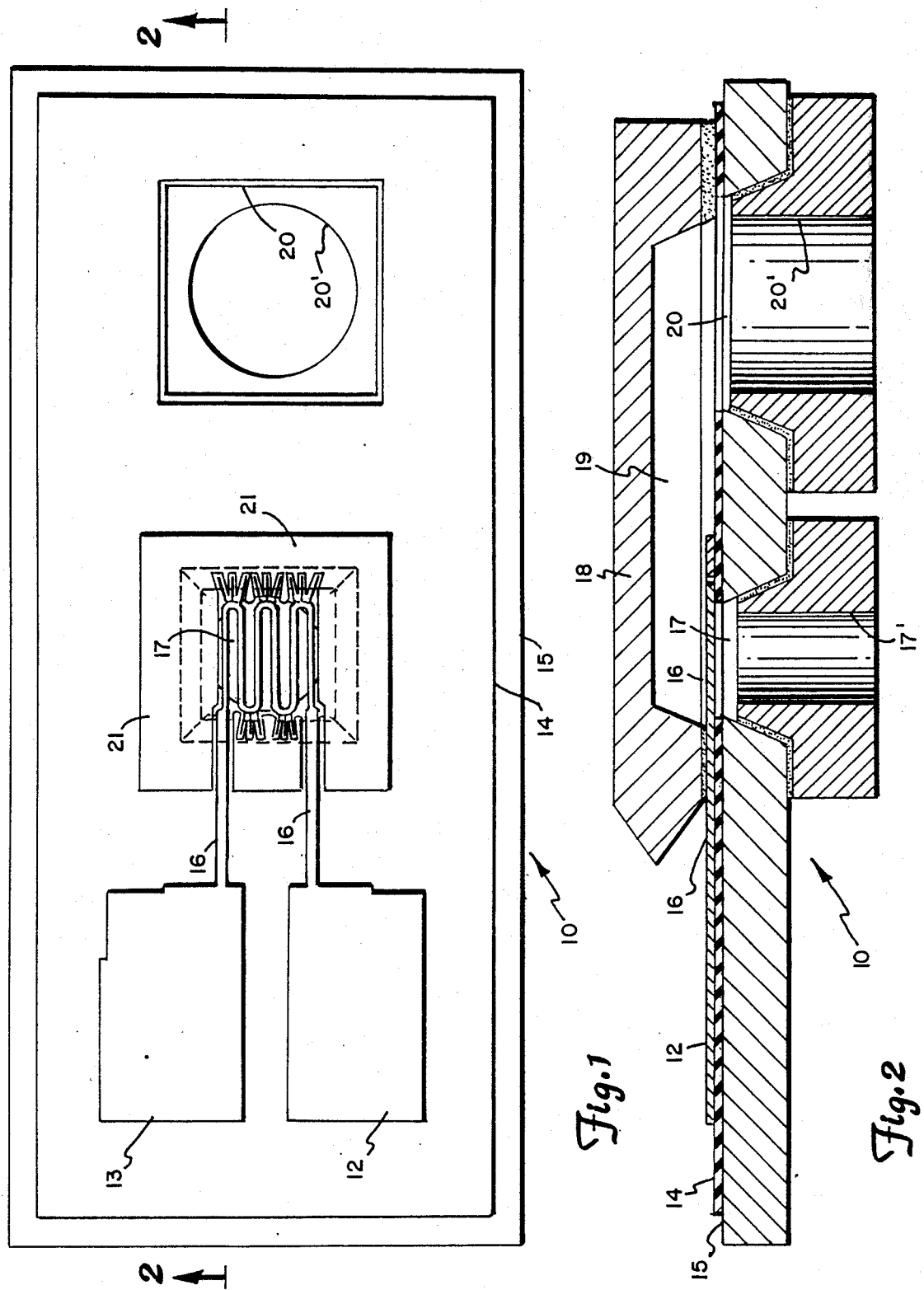

increasing H₂ concentration increasing H₂ concentration

FLUID FLOW DETECTOR

BACKGROUND OF THE INVENTION

Field of the Invention

The present invention relates to detectors of fluid flow effects and, more particularly, to detectors for measuring the mass flow in a flow of gas or the separated constituents in a gas flow.

Fluid flow effects detectors are necessary in many process control situations and in many instrumentation situations. They are used for measuring gas flow in such situations as monitoring heating, ventilation and air conditioning systems, engine intake flows, gas chromatography eluted gas flows, etc.

There are several kinds of detectors used for measuring various aspects of fluid flows. In measuring mass flow rates, for instance, a hotwire anemometer operates by having a heated wire placed across the fluid flow so that the extent of the cooling effect of the fluid on the wire can be measured. Alternatively, a thermistor can be placed in the flowing fluid for this purpose. More recently, various integrated circuit device arrangements supporting a metalization structure in or adjacent the flowing fluid have been used for such measurements to reduce detector size thereby improving sensitivity and, because of batch fabrication techniques, to also reduce detector cost.

There is a need in many mass flow measurement situations for detectors that have a very small thermal mass to reduce the time constants in the detector response to changes in gas flow conditions thereabout. Further, many gas flow situations such as in gas chromatographs have gas flowing in quite small dimension passageways. Thus, a detector structure should correspondingly be adapted for use with such geometrical arrangements.

SUMMARY OF THE INVENTION

The present invention provides a detector of fluid flow effects having a substrate with an opening to accommodate a fluid flow across which a conductor means is suspended without further support of the suspended portion thereof from other structures connected to that substrate. Extensions of a small cross section from such a conductor can be affixed to the substrate to support the suspended portion of the conductive means. A further conductive means can be placed on the suspended conductive means. This further conductive means can serve as a temperature sensor in a feedback loop controlling the current passing through the suspended conductive means to maintain it at a desired temperature. A shroud means cantilevered over the opening and surrounding the suspended conductive means assures fluid flows are confined to passing primarily in the region of the suspended portion of such suspended conductive means.

BRIEF DESCRIPTION OF THE DRAWINGS

FIG. 1 shows a view of the present invention,
FIG. 2 shows a cross section view of FIG. 1.

DESCRIPTION OF THE PREFERRED EMBODIMENTS

Figure 3:
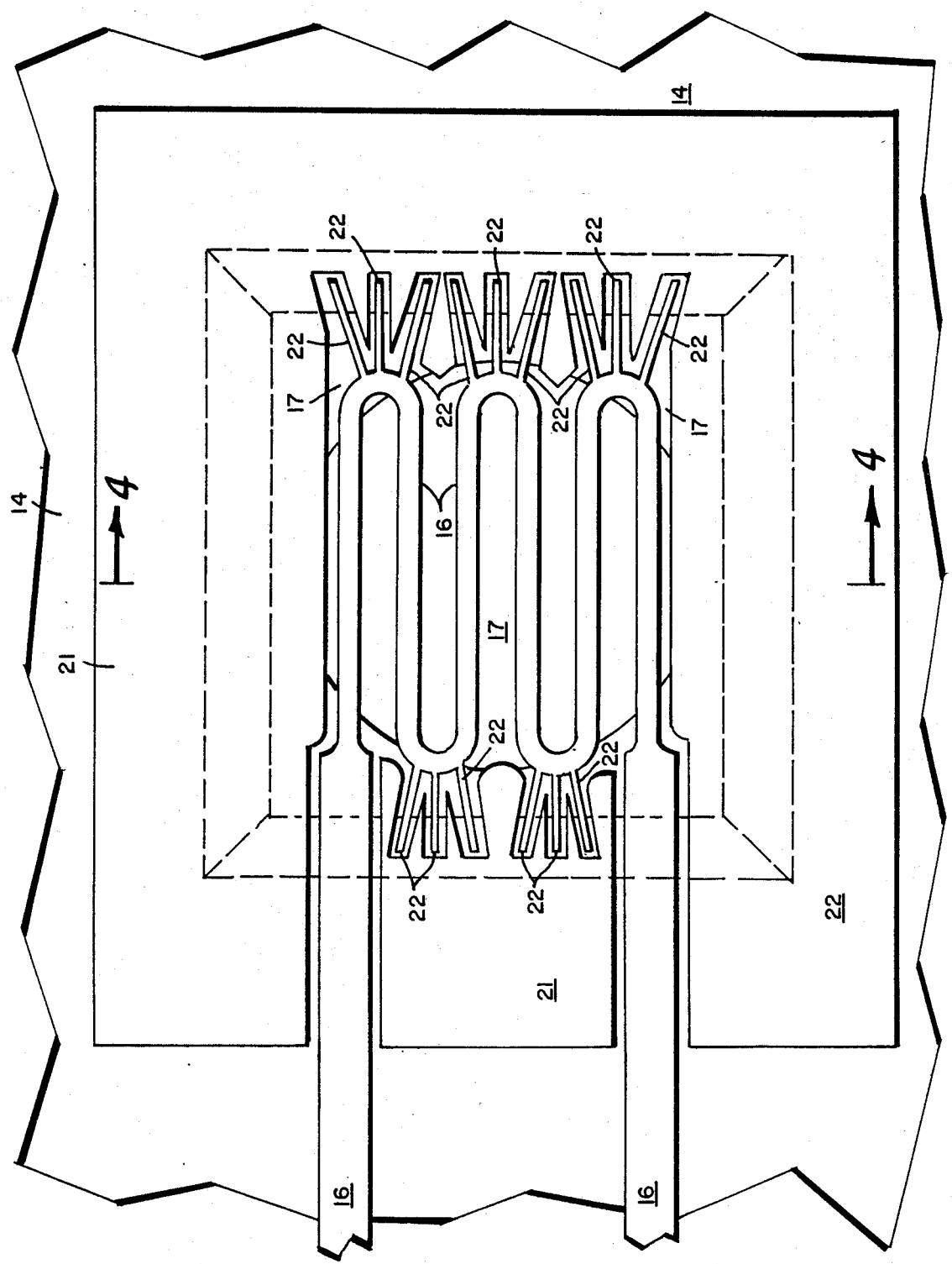
FIG. 3 shows an enlarged view of a portion of FIG. 1.

FIG. 1 shows a view of a major surface of a monolithic integrated circuit chip fluid flow effect sensor, 10. The structure shown is not necessarily drawn to scale or in proportion, but it is rather a representation chosen for clarity.

Sensor 10 is shown in FIG. 1 with two metalization terminals as electrical interconnection regions, 12 and 13, to which external circuits can be electrically interconnected through a convenient interconnection bonding arrangement. These metalization interconnection regions are formed on an insulating layer, 14, formed in turn on a semiconductor material body, 15.

Typically, the semiconductor material body 15 will be formed of p-type conductivity silicon. Insulating layer 14 can be either nitrides of silicon, primarily silicon nitride $Si_3N_4$, or oxides of silicon, primarily silicon dioxide, $SiO_2$. The metal in regions 12 and 13 is formed in a composite layered structure primarily of platinum.

Interconnection regions 12 and 13 are provided in FIG. 1 at opposite ends of an electrically conductive means, 16, having a serpentine shape and formed of the same metalization material as are regions 12 and 13. Conductive means 16 provides the major structure for interacting with flows the effects of which are to be detected. In doing so, conductive means 16 is used as a resistance heater element to primarily raise and maintain its own temperature. Gas flowing thereby conducts heat away from means 16 to a measurable extent which depends on the nature and quantity of the molecules flowing.

Much of conductive means 16 is suspended over an opening, 17, for accommodating a flowing fluid and provided through the substrate supporting means 16 formed by semiconductor material body 15 and insulating layer 14 together. This substrate supports the metalization forming not only means 16 but also interconnection regions 12 and 13. The supporting arrangement of FIG. 1, and opening 17 therethrough, are better shown in FIG. 2, which is a cross section view taken in a direction through the center of FIG. 1.

Note in FIG. 2 that a cover or cap, 18, is shown attached to insulating layer 14, and so to the substrate formed by layer 14 and body 15 together, and over conductive means 16 in FIG. 2. This cap or cover has not been shown in FIG. 1 for purposes of clarity. Cap 18 is formed from silicon semiconductor material and attached to insulating layer 14 through using a glass frit as a bonding material in a well known manner. Use of silicon for cap 18 means it will have a temperature coefficient substantially similar to that of the substrate formed primarily of silicon semiconductor material body 15 to reduce thermal stress on the bond between them.

As can be seen in FIG. 2, there is a suspension portion of conductive means 16 suspended across from or over accommodation opening 17. This suspension portion, other than the support provided by the rest of means 16, is free of any mechanical support of any structure extending thereto from semiconductor material body 15 or insulating layer 14. That is, this suspension portion of conductive means 16 has no other materials between it and opening 17.

This arrangement, resulting in an unsupported suspension portion of conductive means 16, is important in providing a sensitive fluid flow effect detector for fluids flowing thereby after having passed through accommodation opening 17. The elimination of any other materials between conductive means 16 and opening 17, for purposes of providing support to the suspension portion of conductive means 16, results in the minimal amount of thermal mass interacting with the flowing fluid for a selected geometry of conductive means 16. Since detector 10 operates through sensing differences in the ability of flowing fluid to remove heat from conductive means 16, the smaller the mass can be made of the suspension portion of means 16, and any structures immediately thereabout, the smaller the time required for changed conditions in the fluid flowing through opening 17 impinging on conductive means 16 to have an effect thereon by causing temperature changes therein. This, of course, is because smaller masses in general take less time to heat or cool.

Thus, for a gaseous flowing fluid of a constant molecular composition, changes in the mass flow thereof past conductive means 16 can, because of its small mass, be detected more quickly as increases or decreases in the rate at which heat is removed from conductive means 16. This change in rate of heat removal is reflected in changes in temperature of means 16 and so in its electrical resistance. Sensor can be operated in a so-called "constant temperature" mode so that the temperature of the conductive means is controlled to a preselected temperature higher than the ambient temperature, and the electrical power consumed by element 16 is representative of mass flow.

In a gas chromatograph, different eluted gases reach conductive means 16 at different times because of separations thereof in time due to the different partition coefficients of these gases. Each different gas coming along opening 17 is to be detected by conductive means 16. The faster the response of conductive means 16, the more accurately the time separation between gaseous components will be detected. Also, there will be a more accurate measurement of the concentrations of each of the gases through avoiding the averaging of the effects of consecutive eluted gases.

Figure 4:
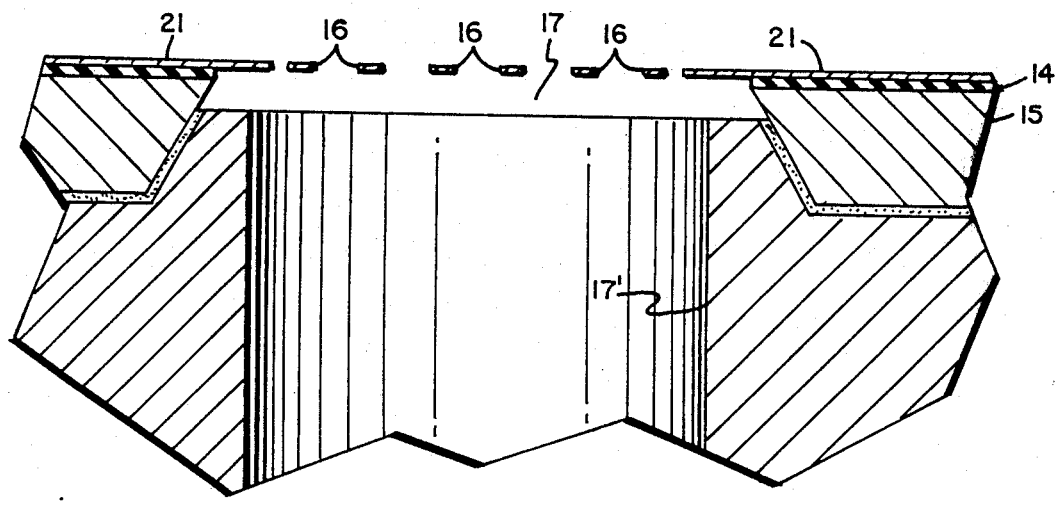
FIG. 4 shows a cross section of the view of FIG. 3.

Cap or cover 18, as shown in FIG. 2, has a recess, 19, therein facing conductive means 16 and opening 17, as well as a further fluid flow accommodation opening, 20. Opening 20 also extends through the substrate formed by insulating layer 14 and semiconductive material body 15. As can be seen by the flow indicating arrows in FIG. 4, flowing gas having effects to be measured is introduced through opening 17, allowed to pass through openings between parts of the suspension portion of conductive means 16 and into recess 19, there to exit sensor 10 through opening 20. The cross section of this low passageway at each point therealong is substantially equal in area more or less perpendicular to the flow direction except at conductive means 16. This avoids having velocity changes occur in the flowing fluid due to passageway cross sectional area differences. Such velocity changes could otherwise affect the results of the sensor thereby reducing its sensitivity.

There is, however, a significant constriction in the flow passageway cross sectional area at the suspension portion of conductive means 16. This constriction, which directs the gas flow along the central axis of accommodation opening 17 perpendicular to the plane parallel to conductive means 16, leads to a certain swirling and turbulence in the flowing gas in the region of conductive means 16. This action in the flowing gas enhances its contact with the suspension portion of conductive means 16 over all of the exposed surfaces thereof. Such good surface contact by the gas with conductive means 16 leads to conductive means 16 responding even more rapidly to changes occurring in flow rate of, or constituent proportions of the flowing gas.

This effect is increased by use of an orifice plate means, 21, to narrow the cross sectional area in which the gas is permitted to flow at conductive means 16 to being concentrated about the suspension portion of means 16. Orifice plate means 21, shown in FIG. 1, is formed of the same metal material and formed at the same time as are interconnection regions 12 and 13 and conductive means 16. Orifice plate means 21 and the suspension portion of conductive means 16 can be better seen in the expanded view of FIG. 3 and the cross section view thereof shown in FIG. 4. FIG. 3 is an expanded view of that portion of FIG. 1 containing the suspension portion of conductive means 16.

As can be seen in FIG. 3, the main current-carrying portions of conductive means 16 over opening 17 have a regular serpentine geometry. There are, in addition, as part of conductive means 16 extension fingers, 22, extending from the more curved parts of the main current-carrying parts of the suspension portion of conductive means 16 to reach and be affixed to insulating layer 14 as supports for this suspension portion over opening 17. Extension fingers 22 have a very much smaller cross sectional area than do the main current-carrying parts of the suspended portion of conductive means 16. This geometrical characteristic of fingers 22 keeps relatively small the amount of heat conducted away from the main current-carrying parts of the suspension portion of means 16 to insulating layer 14.

Further, orifice plate means 21 has cantilevered fingers of its own interspersed between extension fingers 22 to constrict the flow passageway forcing any gas flowing through accommodation opening 17 to primarily pass through the spaces between main current-carrying parts of the suspension portion of conductive means 16. The use of orifice plate 21 thus allows the main current-carrying portions of the suspended portion of conductive means 16 to be placed further from insulating layer 14 and semiconductor material body 15 therebelow to reduce heat loss to these much more massive structures. Despite this substantial spacing between the main current-carrying parts of the suspended portion of conductive means 16 and the substrate, orifice plate means 21 having little thermal mass of its own assures that flowing gas will interact with the main current-carrying parts of the suspension portion of conductive means 16.

Since the cross sectional area of accommodation opening 17 is often dictated by the apparatus to which it is to be mated, the spacing between the main current-carrying parts in the suspension portion of conductive means 16 is determined by the width of those main current-carrying parts. Once these spacings have been determined, the width of the film is set leaving only the thickness thereof to be determined. The ratio of the surface area of these main current-carrying parts to the volume of such parts is desired to be high so that the thermal mass is relatively low for the area over which flowing gas is impinging. The ratio of the thickness of the main current-carrying parts of the suspension portion of means 16 to the width thereof is typically in the range of from 1:50 to 1:500.

Just which thickness is chosen will depend on the application which determines the sensitivity required and on certain practical limitations. Obviously, too thin a film will lead to too little strength to maintain the integrity of the suspended portion of conductive means 16 in operation, as there will be insufficient strength to hold it together sufficiently to support its own weight when heated.

In operation, the main current-carrying parts of the suspended portion in conductive means 16 are heated above the temperature of the flowing fluid, for example, to 650 C. becoming red hot and sagging to some extent from the plane in which they are formed. Note that this sagging of the suspension portion is not restrained by any structure portion, as indicated above, so that the electrical resistance of this portion is, at these elevated temperatures, substantially independent of strain which would be introduced in the suspension portion of conductive means 16 by the substrate.

A further consideration in choosing the metalization thickness that, while less thickness and so less mass, will give a greater sensitivity, there will be an accompanying higher electrical resistance leading to a greater amount of Johnson noise occurring in conductive means 16. Such noise, of course, has the effect of reducing sensitivity. Thus, the particular use to which detector 10 is put must be considered in choosing the thickness for the metalization forming conductive means 16. For one gas chromatograph with an outflow passageway having a diameter of 0.040 in., a preferred ratio for the thickness to width of the main current-carrying part of the suspension portion of means 16 is 160.

FIG. 2 shows a portion of an apparatus using detector 10, the portion shown being two gas flow passageway extension metal tubes, 17' and 20', extending from fluid flow accommodation openings 17 and 20, respectively. Sensor 10 is bonded to extension tubes 17' and 20' by an epoxy resin.

Interconnection regions 12 and 13 are shown and were indicated to be for external circuit connections. Means 16 could be connected to other interconnection regions.

The fabrication of sensor 10 begins with a p-type conductivity crystalline silicon wafer for semiconductor material body 15. Body 15 has a nitride or oxide layer, to serve as insulating layer 14, on a major surface thereof in the (100) crystal plane. Such an insulating layer is grown thereon by well known methods to a thickness of approximately 1,500 A (Angstrom). Next, electrical interconnection regions 12 and 13, conductive means 16, and orifice plate means 21 are all formed simultaneously from a metal deposition using well know deposition methods. This deposition is begun with first depositing about 200 A of nichrome or titanium as an adhesion base followed by depositing pure platinum thereon of a thickness determined in part by the use to which it is to be put, but typically from 2,000 A to 10,000 A. Using well known photolithographic and lift-off methods, the deposited metal composite layer is partially removed to form the structures shown for interconnection regions 12 and 13, conductive means 16 and orifice plate means 21. Conductive means 16 is centered in sensor 10 to further reduce stress effects.

Thereafter, semiconductor material body 15, as part of the wafer, is etched anisotropically from the side opposite that upon which the foregoing metal deposition was made using the etchant potassium hydroxide (KOH) with standard methods to form the basis for openings 17 and 20 in that semiconductor material. A similar etch process can be used to provide recess 19 in cap 18.

This etch of body 15 is followed with a standard method dip etch to remove insulator 14 from where openings 17 and 20 are to occur and from under the suspension portion of conductive means 16. If layer 14 is of nitride, these portions can be removed by a plasma etch or by phosphoric acid ($H_3PO_4$) with such an etch leaving the deposited metal in conductive means 16 and orifice plate means 21 relatively unaffected. For an oxide, the dip etch can be performed by hydrofluoric acid (HF) again leaving conductive means 16 and orifice plate means 21 relatively unaffected. Note that the insulator layer dip etch proceeds with insulating material 14 etched from both sides where it would occur in what are to be openings 17 and 20. As a result, the insulating material is removed much more quickly here than it will be where it is located over semiconductor material 15 and other portions of sensor 10.

In some applications, chemical reactions take place between gases or vapors as they pass through the detector. These reactions can be accelerated by contact with the heated conductive means 16 when the conductive means 16 is formed of a catalytic material such as platinum. Heat produced by catalytic action will reduce the accuracy of the measurement. To avoid this catalytic action problem, the exposed surfaces of conductive means 16 are coated with a passivating layer which reduces or eliminates direct contact between the catalyst and the fluid, effectively stopping the catalysis. The passivating layer can be made thin in order to avoid excessive thermal mass or high thermal resistance between the element and the fluid. The passivating layer is formed preferably of silicon dioxide ($SiO_2$) deposited by chemical vapor deposition (CVD) using tetraethyl orthosilicate (TEOS). The conductive means 16 supports the thin passivation layer which is deposited after etching away of the relatively thick thermal oxide 14 and the substrate 15.

Figure 6:
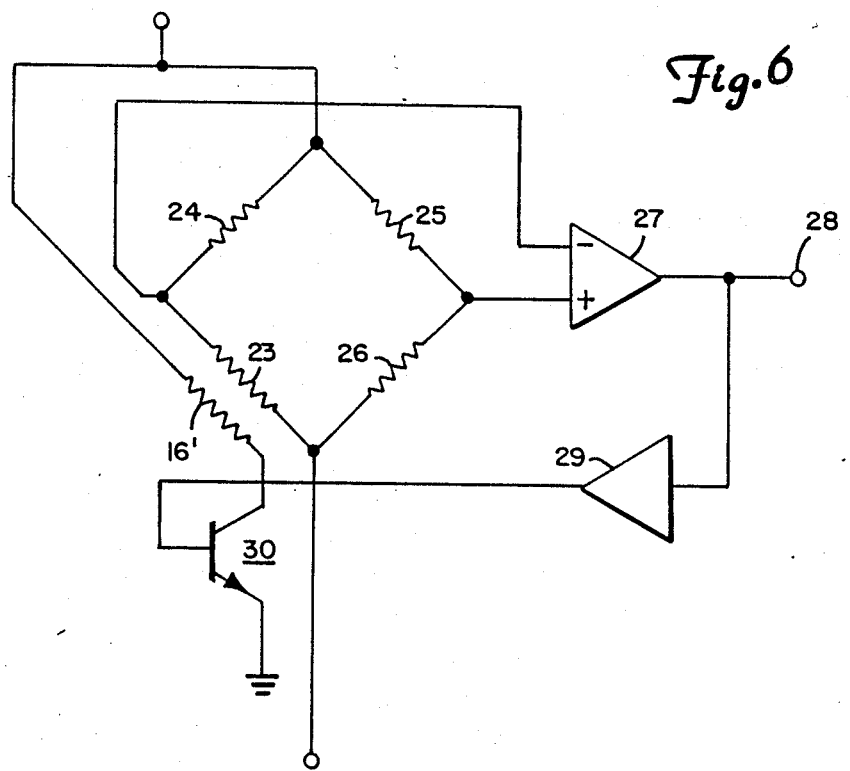
FIG. 6 shows a circuit schematic diagram for use with the alternative embodiment shown in FIG. 5.
Figure 5:
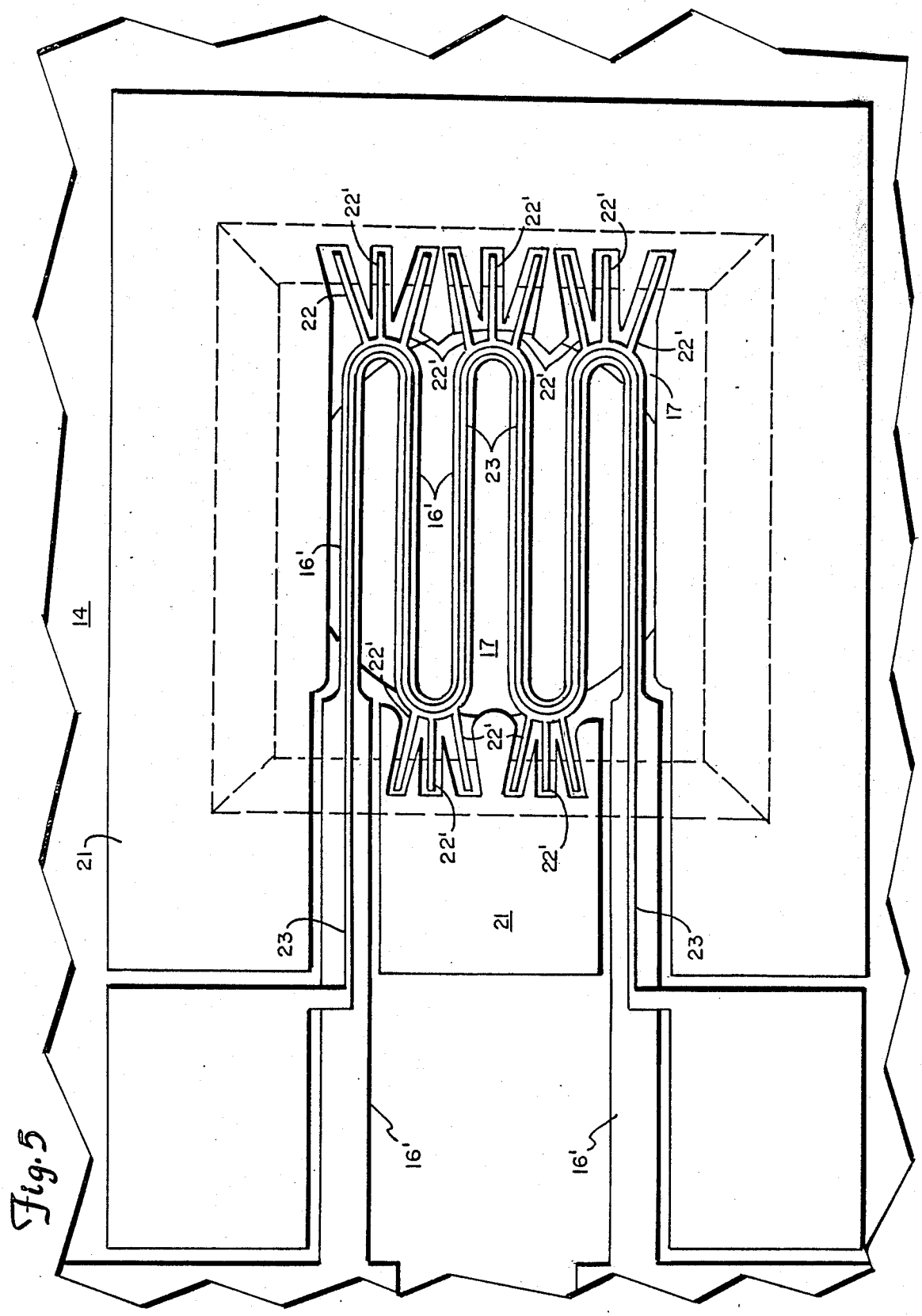
FIG. 5 shows an alternative embodiment of the present invention based on the structural portion shown in FIG. 3.

An alternative embodiment of the present invention is shown in FIG. 5 where conductive means 16 has been redesignated 16' and extension fingers 22 have been redesignated 22' to reflect that (i) a 200 A nichrome layer has been provided on the upper surface of means 16, and (ii) a 1500 A insulative layer of either silicon nitride or silicon dioxide has been deposited on this nichrome layer. This is followed by providing a second composite nichrome and platinum layer, 23, on the last insulating layer to serve as a supplemental conductive means to be used as a resistance based temperature sensor. Layer 23 can again be 1500 A but will usually be chosen to be considerably thinner to reduce the thermal mass present which is possible because layer 23 is supported by means 16'. Such an arrangement permits use of the sensing-control system shown in FIG. 6. Supplemental conductive means 23 is included in a bridge circuit to be provided between positive and negative voltage supplies at the small, open circle terminals shown. This bridge circuit has therein further resistors 24, 25 and 26 which are provided at a stable temperature as reference resistance values.

Thus, if the temperature of conductive means 16' should change because, for instance, of an increase in gas flow thereby, there will be a corresponding change in the temperature and electrical resistance of supplemental conductive means 23. This change in resistance will lead to a change in the voltage across the bridge between the two inputs of a differential averaging means 27. Differential averaging means 27 will provide a signal at its output, 28, which is an average of the signal developed across the bridge containing supplemental conductor means 23 and resistors 24 through 26.

This same output signal will be used to drive a buffer means, 29, which in turn drives the base of an npn bipolar transistor, 30. Thus, the signal at output 28 is used to control the amount of current transistor 30 permits to be drawn through conductive means 16' to thereby control its temperature. Hence, in the feedback system of FIG. 6, changes in temperature occurring in conductive means 16' because of varying fluid flow conditions are counteracted by the action in the feedback loop of FIG. 6 to maintain conductive means 16' at a preselected temperature. The average signal required to do this is present at system output 28 and therefor its value is a measure of the heat transfer effect of the flowing gas on conductive means 16'.

Since supplemental conductive means 23 can carry a much smaller current because such a current need not be sufficient to provide any of the heating of conductive means 16', this arrangement leads to sensing the condition with a much smaller Johnson noise component occurring therewith because of the reduced current through supplemental conductive means 23. This improves the sensitivity of the detector.

Figure 7A:
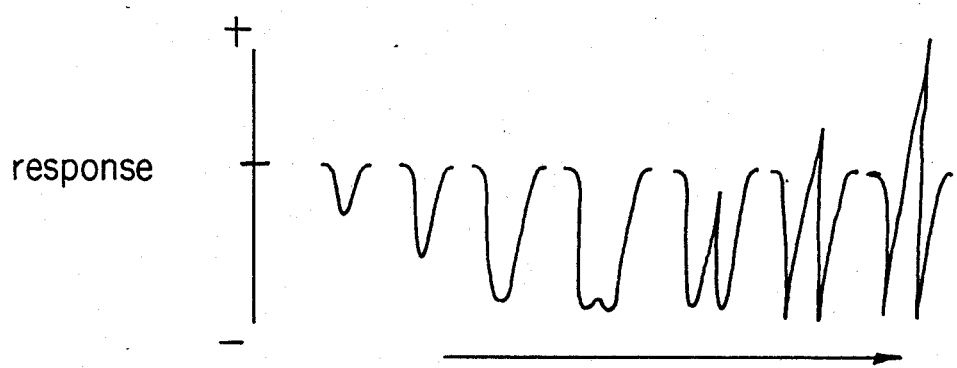
FIG. 7A shows the performance of a PRIOR ART sensor detecting hydrogen in a helium carrier.
Figure 7B:
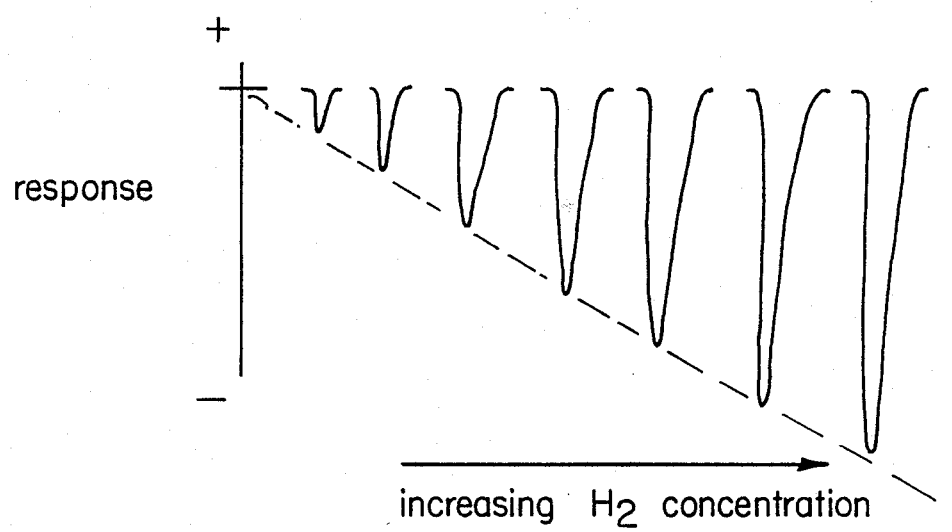
FIG. 7B shows the performance of a sensor according to the present invention detecting hydrogen in a helium carrier.

The sensor is particularly suited for sensing concentration of hydrogen gas in a helium carrier gas. In some existing detectors, hydrogen gas in a helium carrier produces a nonlinear output amplitude (power consumption, for example) as a function of the hydrogen gas concentration, particularly when the hydrogen concentration exceeds about 8%. With the present invention, it is found that the response of the sensor to hydrogen in a helium carrier has improved linearity. In FIG. 7B, the time response of a sensor according to the present invention is shown as a function of hydrogen gas concentration. In FIG. 7A, the time responses of a prior art sensor are shown for comparison. The sensor of the present invention provides a substantially linear response while the prior art sensor provides outputs which are non-linear and change polarity, as well, making measurement difficult.

The sensor can be used in applications where substantially no flow of fluid is provided to the sensor, that is, the sensor can be placed in a substantially stagnant body of fluid for sensing the thermal conductivity of the fluid. The thermal conductivity of the fluid affects the rate at which heat or power is conducted away from the heated conducting means 16. The power consumption of the sensor is thus representative of the thermal conductivity of the fluid.

Although the present invention has been described with reference to preferred embodiments, workers skilled in the art will recognize that changes may be made in form and detail without departing from the spirit and scope of the invention.

What is claimed is:

1. A thermal mass flow sensing device, said device comprising:
   a substrate having first and second major surfaces on opposite sides thereof with there being a first accommodation opening in said first major surface extending to the second major surface, said substrate comprising a semiconductor material;
   first and second electrical interconnection regions on said substrate first major surface; and
   a suspended conductor capable of conducting electrical current therethrough between first and second ends thereof with said first end in electrical contact with said first electrical interconnection region and with said second end being in electrical contact with said second electrical interconnection region, said suspended conductor having a suspension portion thereof with a major surface substantially aligned parallel to the first major surface of the substrate and disposed between said first and second ends of the suspended conductor and with an integral extension therefrom affixed to said substrate, wherein the suspension portion is self-supporting and suspends itself across the first accommodation opening such that mass flows through the first accommodation opening substantially transverse to the major surface of the suspension portion.

2. The apparatus of claim 1 wherein said suspension portion of said suspended conductor follows a serpentine shape.

3. The apparatus of claim 1 wherein said extension has a smaller cross section area than said main current carrying part of said suspension portion of said suspended conductor means.

4. The apparatus of claim 3 wherein said suspension portion of said suspended conductor has a plurality of extensions from a main current carrying part thereof affixed to said substrate.

5. A thermal mass flow sensing device, said device comprising:
   a substrate having first and second major surfaces on opposite sides thereof with there being a first accommodation opening in said first major surface extending to the second major surface and a second accommodation opening for fluid flow in said first major surface, said substrate comprising a semiconductor material;
   first and second electrical interconnection regions on said substrate first major surface;
   a suspended conductor means capable of conducting electrical current therethrough between first and second ends thereof with said first end in electrical contact with said first electrical interconnection region and with said second end being in electrical contact with said second electrical interconnection region, said suspended conductor means having a suspension portion thereof with a major surface substantially aligned parallel to the first major surface of the substrate and disposed between said first and second ends of the suspended conductor means, wherein the suspension portion is self-supporting and suspends itself across the first accommodation opening such that mass flows through the first accommodation opening substantially transverse to the major surface of the suspension portion; and
   wherein a cap means having a recess therein is affixed to said substrate first major surface with said recess facing both said first and second accommodation openings such that a fluid flow can flow from one of such openings to that other one remaining through said recess.

6. The apparatus of claim 5 wherein said suspension portion of said suspended conductor has an extension from a main current carrying part thereof affixed to said substrate.

7. A thermal mass flow sensing device, said device comprising:

a substrate having first and second major surfaces on opposite sides thereof with there being a first accommodation opening in said first major surface, said substrate comprising a semiconductor material;

first and second electrical interconnection regions on said substrate first major surface;

a suspended conductor means capable of conducting electrical current therethrough between first and second ends thereof with said first end in electrical contact with said first electrical interconnection regions and with said second end being in electrical contact with said second electrical interconnection region, said suspended conductor means having a suspension portion thereof located between said first and second ends thereof which is suspended across said first accommodation opening free of any structure located between said suspension portion and said first accommodation opening that is mechanically connected to said substrate to thereby support said suspension portion, whereby any fluid in said first accommodation opening can directly impinge on said suspension portion; and an orifice plate means supported on said substrate first major surface cantilevered over said first accommodation opening to be adjacent to said suspension portion of said first suspended conductor means.

8. The apparatus of claim 7 wherein said orifice plate means though free of any mechanical contact with said suspended conductor means is substantially cantilevered over said first accommodation opening peripherally about said suspended conductor means.

9. A thermal mass flow sensing device, said device comprising:

a substrate having first and second major surfaces on opposite sides thereof with there being a first accommodation opening in said first major surface, said substrate comprising a semiconductor material;

first, second, third and fourth electrical interconnection regions on said substrate first major surface;

a suspended conductor means capable of conducting electrical current therethrough between first and second ends thereof with said first end in electrical contact with said first electrical interconnection region and with said second end being in electrical contact with said second electrical interconnection region, said suspended conductor means having a suspension portion thereof located between said first and second ends thereof which is suspended across said first accommodation opening free of any structure located between said suspension portion and said first accommodation opening that is mechanically connected to said substrate to thereby support said suspension portion, whereby any fluid in said first accommodation opening can directly impinge on said suspension portion; and a supplement conductor means capable of conducting electrical current therethrough between first and second ends thereof with said first end in electrical contact with said third electrical interconnection region and with said second end being in electrical contact with said fourth interconnection region, said supplement conductor means having an intermediate portion thereof between said first and second ends thereof being affixed to said suspension portion of said suspended conductor means.

10. The apparatus of claim 9 wherein said supplement conductor means is electrically connected in a resistance measuring circuit that is electrically connected to a current controller which is electrically connected to said suspended conductor means such that a sufficient change in resistance of said supplement conductor means leads to a change in current through said suspended conductor means.

11. The apparatus of claim 9 wherein said supplement conductor means and said suspended conductor means are separated by an electrical insulating layer.

12. The apparatus of claim 10 wherein said resistance measuring circuit is a bridge circuit formed of two strings of series connected resistive elements which strings are electrically connected at each end thereof to one of a pair of terminal means, one at each end of each said string, and each said terminal means being adapted for electrical connection to a source of voltage, there being two of said resistive elements in each string electrically connected to each other at a sensing junction, said current controller having first and second inputs each connected to one of said sensing junctions, said current controller providing an output signal representative of that current said current controller is drawing through said suspended conductor means.

13. A thermal mass flow sensing device, said device comprising:

a substrate having first and second major surfaces on opposite sides thereof with there being a first accommodation opening in said first major surface, said substrate comprising a semiconductor material;

first and second electrical interconnection regions on said substrate first major surface; and a suspended conductor means capable of conducting electrical current therethrough between first and second ends thereof with said first end in electrical contact with said first electrical interconnection region and with said second end being in electrical contact with said second electrical interconnection region, said suspended conductor means having a suspension portion thereof located between said first and second ends thereof which is suspended across and first accommodation opening free of any structure located between said suspension portion and said first accommodated opening that is mechanically connected to said substrate to thereby support said suspension portion, and with said suspension portion having an extension from a main current carrying part thereof affixed to said substrate that has a smaller cross section area than said main current carrying part thereof, whereby any fluid in said first accommodation opening can directly impinge on said suspension portion.

* * * * *

UNITED STATES PATENT AND TRADEMARK OFFICE
CERTIFICATE OF CORRECTION

PATENT NO. : 4,909,078
DATED : March 20, 1990
INVENTOR(S) : Fred C. Sittler et al.

It is certified that error appears in the above-identified patent and that said Letters Patent is hereby corrected as shown below:

```
        Col. 3, line 32, delete "Sensor", insert
--Sensor 10--
        Col. 9, line 22, delete "regions", insert
--region--
        Col. 10, line 19, after "current", insert
--drawn--
        Col. 10, line 58, delete "accommodated", insert
--accommodation--
```

Signed and Sealed this

Tenth Day of September, 1991

Attest:

HARRY F. MANBECK, JR.

Attesting Officer

Commissioner of Patents and Trademarks